(12) United States Patent
Zorner et al.

(10) Patent No.: US 12,329,162 B2
(45) Date of Patent: **\*Jun. 17, 2025**

(54) METHODS FOR ENHANCING ROOT STRENGTH AND SAFETY OF TURF GRASS

(71) Applicant: Locus Solutions IPCo, LLC, Solon, OH (US)

(72) Inventors: Paul S. Zorner, Encinitas, CA (US); Tyler Dixon, Kent, OH (US); Sean Farmer, Ft. Lauderdale, FL (US); Ken Alibek, Solon, OH (US); Caleb Adkins, Solon, OH (US); Alex Fotsch, San Diego, CA (US); Samal Ibragimova, Solon, OH (US)

(73) Assignee: LOCUS SOLUTIONS IPCO, LLC, Solon, OH (US)

( * ) Notice: Subject to any disclaimer, the term of this patent is extended or adjusted under 35 U.S.C. 154(b) by 790 days.

This patent is subject to a terminal disclaimer.

(21) Appl. No.: 17/264,832

(22) PCT Filed: Apr. 21, 2020

(86) PCT No.: PCT/US2020/029091
§ 371 (c)(1),
(2) Date: Jan. 31, 2021

(87) PCT Pub. No.: WO2020/219432
PCT Pub. Date: Oct. 29, 2020

(65) Prior Publication Data
US 2022/0030878 A1    Feb. 3, 2022

Related U.S. Application Data

(60) Provisional application No. 62/846,875, filed on May 13, 2019, provisional application No. 62/836,902, filed on Apr. 22, 2019.

(51) Int. Cl.
*A01N 63/22* (2020.01)
*A01G 7/06* (2006.01)
*A01G 20/00* (2018.01)

(52) U.S. Cl.
CPC ............... *A01N 63/22* (2020.01); *A01G 7/06* (2013.01); *A01G 20/00* (2018.02)

(58) Field of Classification Search
CPC .......... A01N 63/22; A01G 7/06; A01G 20/00; C12R 2001/07; C12R 2001/885;
(Continued)

(56) References Cited

U.S. PATENT DOCUMENTS 8,598,083 B2    12/2013    Kaminskyj et al.
9,416,061 B2    8/2016    Johnson
(Continued)

FOREIGN PATENT DOCUMENTS

CA    3099285 A1    11/2019
CA    3175391 A1    10/2021
(Continued)

OTHER PUBLICATIONS

Athletic Turf News <https://athleticturf.net/field-safety-best-practices/> 2018. (Year: 2018).*
(Continued)

*Primary Examiner* — Scarlett Y Goon
*Assistant Examiner* — Sarah C Wistner
(74) *Attorney, Agent, or Firm* — SALIWANCHIK, LLOYD & EISENSCHENK (57) ABSTRACT

Methods are provided for enhancing the health, growth and/or sturdiness of turf grasses by applying a combination of microbes and/or their growth by-products to the turf grass roots and/or to soil. Specifically, in one embodiment, the subject invention utilizes *Trichoderma harzianum* and a strain of *Bacillus amyloliquefaciens*. The methods can fur-
(Continued)

ther be used to improve maintenance and upkeep of natural turf grass fields used in, for example, athletics and recreation, as well as to increase the functionality and safety of these natural turf grass fields.

18 Claims, 5 Drawing Sheets

(58) Field of Classification Search
CPC .......... Y02W 30/40; C05F 11/08; C12N 1/14; C12N 1/20; C12N 1/205
See application file for complete search history.

(56) References Cited

U.S. PATENT DOCUMENTS

| | | | |
|---|---|---|---|
| 11,447,430 B2 * | 9/2022 | Zorner | A01N 63/22 |
| 2005/0096225 A1 | 5/2005 | Johnson | |
| 2008/0318777 A1 | 12/2008 | Lin et al. | |
| 2010/0143316 A1 | 6/2010 | Hsieh et al. | |
| 2011/0274673 A1 | 11/2011 | Kang et al. | |
| 2012/0096598 A1 | 4/2012 | Harman | |
| 2013/0202562 A1 | 8/2013 | Wood | |
| 2013/0205849 A1 | 8/2013 | Kloepper et al. | |
| 2013/0276493 A1 * | 10/2013 | Johnson | C05B 15/00 71/8 |
| 2016/0040119 A1 | 2/2016 | Hashman | |
| 2016/0186273 A1 | 6/2016 | Taghavi et al. | |
| 2016/0345588 A1 | 12/2016 | Johnson | |
| 2017/0223956 A1 | 8/2017 | Habib et al. | |
| 2018/0242511 A9 | 8/2018 | Fabbri et al. | |
| 2019/0174692 A1 | 6/2019 | Harman et al. | |

FOREIGN PATENT DOCUMENTS

| | | | | |
|---|---|---|---|---|
| JP | H0248486 A | 2/1990 | | |
| WO | 2016063305 A2 | 4/2016 | | |
| WO | 2017089641 A1 | 6/2017 | | |
| WO | 2017174503 A1 | 10/2017 | | |
| WO | 2018094075 A1 | 5/2018 | | |
| WO | WO-2018183976 A1 * | 10/2018 | | A01C 1/06 |
| WO | 2019012541 A1 | 1/2019 | | |
| WO | 2019133923 A1 | 7/2019 | | |
| WO | 2019217548 A1 | 11/2019 | | |
| WO | 2021211548 A1 | 10/2021 | | |

OTHER PUBLICATIONS

Ross et al. (Ann. Appl. Biol. (1991), 118, 433443. (Year: 1991).*
"Arbico Organics" webpage <https://www.arbico-organics.com/>, pp. 1-6, May 13, 2017, retrieved from Internet Archive Wayback Machine <https://web.archive.org/web/20170513062856/https://www.arbico-organics.com/product/terragrow-microbial-amendment/organic-soil-conditioners> on Mar. 3, 2025. (Year: 2017).*
Locus: "Rhizolizer (TM) Soil Amendment." Retrieved from Internet: Mar. 9, 2018, <<https://locusag.com/wp-content/uploads/2018/3/Locus_AG_Rhizolizer_labels_FLORIDA.pdf>> pp. 1-2.
Baltzoi, P., et al., "Effect of Symbiotic Microorganisms on Turfgrass Under Two Irrigation Regimes." International Journal of Plant & Soil Science, 2015, 8(2): 1-9.
Patakioutas, G., et al., "Turfgrass Root System Inoculation and Colonization by a Mycorrhizal Fungus and other Symbiotic Micro-Organisms and Evaluation of its Effects on Green Turf Cover and Growth." XXIX International Horticultural Congress on Horticulture: Sustaining Lives, Livelihoods and Landscapes, 2014, 1122: 65-72.
Peters, A. These probiotics for plants help farms suck up CO2—Fast Company. FASTCOMPANY . https://www.fastcompany.com/90303108/these-probiotics-for-plants-help-farms-suck-up-extra-carbon-dioxide (Feb. 7, 2019): 1-6.
Aboud, H,M., et al., "Interaction of Bacillus Subtilis and Trichoderma Harzianum with Mycorrhiza on Growth and Yield of Cucumber (*Cucumis sativus* L.)." International Journal of Current Research, 6.8 (2014): pp. 7754-7758.
Alexis, Z.P., et al., "Effect of soil amendment with Trichoderma harzianum and Bacillus amyloliquefaciens bioformulation on biochemical parameters and antioxidant activity in Abelmoschus esculentus." International Journal of Innovation and Applied Studies, 33.3 (2021): pp. 522-535.
De Boer, W., et al., "Living in a fungal world: impact of fungi on soil bacterial niche development." FEMS Microbiology Reviews, 29.4 (2005): pp. 795-811.
Locus Agriculture, "Unique 'Probiotic' For Crops Receives Expanded Regulatory Approvals." News release, Aug. 9, 2018, retrieved from << URL:https://locusag.com/news-releases/unique-probiotic-for-crops-receives-expanded-regulatory-approvals/ >>, pp. 1-4.
Malusa, E., et al., "Technologies for Beneficial Microorganisms Inocula Used as Biofertilizers." The Scientific World Journal, 2012.491206 (2012): pp. 1-12.
Passoth, V., et al., "Past, present and future research directions with Pichia anomala." Antonie van Leeuwenhoek, 99 (2011): pp. 121-125.
Samaniego-Gamez, B.Y., et al., "*Bacillus* spp. inoculation improves photosystem II efficiency and enhances photosynthesis in pepper plants." Chilean Journal of Agricultural Research, 76.4 (2016): pp. 409-416.
Vinale, F., et al., "Harzianic Acid, an Antifungal and Plant Growth Promoting Metabolite from Trichoderma harzianum." Journal of Natural Products, 72.11 (2009): pp. 2032-2035.
Wu, S., et al., Mitigation of nitrous oxide emissions from acidic soils by Bacillus amyloliquefaciens, a plant growth-promoting bacterium. Global Change Biology, 24.6 (2018): pp. 2352-2365.

* cited by examiner

METHODS FOR ENHANCING ROOT STRENGTH AND SAFETY OF TURF GRASS

CROSS-REFERENCE TO RELATED APPLICATION

This application is a National Stage Application of International Application No. PCT/US2020/029091, filed Apr. 21, 2020; which claims priority to U.S. Provisional Patent Application Nos. 62/836,902, filed Apr. 22, 2019, and 62/846,875, filed May 13, 2019, all of which are incorporated herein by reference in their entirety.

BACKGROUND OF THE INVENTION

A wide variety of athletic, recreational and entertainment venues utilize fields planted with turf grasses. Turf grasses, such as Kentucky bluegrass, Bent grass and Bermuda grass, are narrow-leaved grass species that grow and form a uniform ground cover. These species can typically tolerate being treaded on and being pruned or mowed to heights of, for example, a few inches or less.

The structure of turf grasses makes them ideal plants for athletics and recreation. The plants form horizontal stems, called stolons and rhizomes, that creep laterally above and below the ground, sprouting new plants and roots as they grow. Additionally, the lateral growth allows for cutting the grass as sod and rolling or stacking it so that it can be transported with ease.

An important aspect of turf grass health and sturdiness is the health of the root structure. The rhizosphere is the zone of soil wherein a plant's root system grows and absorbs water and nutrients. The amount of nutrients and water the roots absorb depends on, for example, the number of roots, depth of roots, and the characteristics of the soil. Turf grass root growth can also be affected by, for example, temperature, oxygen, pH and pests.

The typical rooting depth for turf grasses can range from about 2 inches to 6 inches. As resources at the soil surface are depleted, roots begin using up resources that are deeper in the soil. A well-developed and actively-growing root system can take advantage of these deeper resources.

Root health and growth also depend on the health of the particular microbiome that exists within the soil. Soils contain billions of different microorganisms, which coexist with each other and with plants to form a complex network of relationships. Among other things, the soil microbiome can help fight off soil-borne pests and can improve conditions for plant growth and health.

Because of, for example, the wear and tear that an athletic or recreational field, course or track can incur, turf maintenance is important; however, maintenance can be costly and burdensome. Groundskeepers must consistently monitor and implement mowing, watering, pest and weed control, fertilization, reseeding and fixing of holes and divots.

A poorly maintained field, course or track can lead to a variety of problems. For example, uneven ground, divots and holes can cause injuries due to tripping and twisted ankles. Imperfections can also impact the outcome of an athletic event by, for example, affecting the way a ball moves or bounces across the ground. Furthermore, pests and weeds that inhabit the grass can be a nuisance, leading to, for example, allergic reactions or bites.

Groundskeepers often rely on the use of chemical fertilizers and pesticides to encourage growth as well as protect turf from pests, weeds and environmental conditions, such as drought or poor soil nutrient content. As potential sources of pollution, responsible use of these substances is an ecological and commercial imperative. Over-dependence and long-term use of these chemicals can alter soil ecosystems, reduce stress tolerance, increase the prevalence of resistant pests, and impede plant growth and vitality. Furthermore, use of these chemicals on fields can be harmful to humans and animals that may inhale or otherwise come into contact with them.

One way in which groundskeepers have tried to reduce the cost of maintaining athletic complexes and fields has been to install artificial, or synthetic, turf fields. While easier and cheaper to care for, artificial fields typically have harder surfaces than natural turf fields, causing increased soreness and fatigue for users, as well as increased risk for concussion and injuries in the case of falls or collisions. Additionally, the synthetic fibers of the turf, along with rubber infill granules spread with the turf, can wear over time and be washed into the environment. The runoff can drain into water sources and cause pollution. Furthermore, the surfaces of artificial turf fields are known to reach temperatures significantly hotter than natural grass fields, where transpiring grass leaves are cooled by release of water vapor and evaporation.

Due to the disadvantages of artificial turf, natural turf grasses are preferred over artificial fields for use in athletics and recreation; however, improved methods for maintaining natural turf grass fields are needed.

BRIEF SUMMARY OF THE INVENTION

The subject invention relates to care and maintenance of turf grasses in, for example, athletics and recreational settings. More specifically, the subject invention provides methods for enhancing the health, growth and sturdiness of turf grass. Advantageously, the methods are low-cost, utilize non-toxic substances, and can be implemented with ease by grounds-keeping employees with minimal additional training.

In one embodiment, the methods comprise applying a soil treatment composition to the roots of the grass and/or to the soil in which the grass grows. In one embodiment, the soil treatment composition comprises one or more microorganisms, growth by-products thereof, and, optionally, one or more sources of nutrients.

In preferred embodiments, the microorganism is a non-pathogenic bacterium, yeast and/or fungus selected from, for example, *Trichoderma* spp., *Bacillus* spp., *Wickerhamomyces anomalus, Myxococcus xanthus, Pseudomonas chlororaphis, Starmerella bombicola, Saccharomyces boulardii, Pichia occidentalis, Pichia kudriavzevii, Meyerozyma guilliermondii*, mycorrhizal fungi, nitrogen fixers (e.g., *Azotobacter vinelandii*) and/or potassium mobilizers (e.g., *Frateuria aurantia*).

The species and ratio of microorganisms and other ingredients in the composition can be determined according to, for example, the species of grass being treated, the soil type where the turf is growing, the health of the turf at the time of treatment, as well as other factors. Thus, the composition can be customizable for any given turf field.

In one embodiment, the amount of each microorganism is at least $1\times10^9$ cells/g of the composition in dried form, including up to $1\times10^{10}$, $1\times10^{11}$, $1\times10^{12}$ and even up to $1\times10^{13}$ cells/g.

In certain embodiments, the soil treatment composition comprises a first microorganism and a second microorganism, growth by-products thereof, and, optionally, one or more sources of nutrients. In a specific embodiment, the first microorganism is *Trichoderma harzianum* and the second microorganism is *Bacillus amyloliquefaciens* (e.g., *B. amyloliquefaciens* NRRL B-67928).

In one embodiment, the composition can comprise from 1 to 99% *Trichoderma* culture by volume and from 99 to 1% *Bacillus* culture by volume. In preferred embodiments, the cell count ratio of *Trichoderma* to *Bacillus* is about 1:4.

The microorganisms of the subject soil treatment compositions can be obtained through cultivation processes ranging from small to large scale. These cultivation processes include, but are not limited to, submerged cultivation/fermentation, solid state fermentation (SSF), and modifications, hybrids and/or combinations thereof. In preferred embodiments, the microbes are cultivated using SSF or modifications thereof.

In one embodiment, the soil treatment composition further comprises microbial growth by-products, which can include, for example, the fermentation medium in which the microbes were cultivated, and/or any leftover nutrients from cultivation. The growth by-products can further include metabolites or other biochemicals produced as a result of cell growth, including, for example, biosurfactants, enzymes and/or solvents.

The methods can further comprise adding materials to enhance microbe growth during application (e.g., adding nutrients to promote plant and/or microbial growth). In one embodiment, the nutrient sources can include, for example, sources of magnesium, phosphate, nitrogen, potassium, selenium, calcium, sulfur, iron, copper, zinc, proteins, vitamins and/or carbon.

In one embodiment, the method further comprises applying one or more prebiotics with the soil treatment composition. For example, suitable probiotics can include one or more of kelp extract, fulvic acid, chitin, humate and humic acid.

In some embodiments, the method of the subject invention further comprises applying additional components, such as, for example, herbicides, fertilizers, pesticides and/or soil amendments. Preferably, the additional components are non-toxic and environmentally-friendly. The exact materials and the quantities thereof can be determined by a groundskeeper or a turf scientist having the benefit of the current disclosure.

In one embodiment, the method enhances the health, growth and sturdiness of turf grass by enhancing the strength of the root system. In certain embodiments, enhanced root strength comprises increased tensile strength of a root or root system, meaning increased ability to resist breaking under tension. In certain embodiments, enhanced root strength comprises increased tensile strength of a sheet of sod. Root strength can be enhanced by, for example, increasing root numbers and/or density, as well as increasing the diameter and rooting depth of individual roots.

In certain embodiments, the methods of the subject invention further comprise testing the grass for root strength after treatment with the soil treatment composition. Testing can include, for example, determining the root tensile breaking force of a grass plant root and/or root system, and/or testing the tensile breaking force required to tear a sheet of sod in two pieces.

In one embodiment, by enhancing the health, growth and sturdiness of turf grass through increased root strength, the methods improve the ability of the grass plants to remain anchored in soil without being uplifted or carved out due to the activities being conducted thereon. For example, the methods can be used to reduce the number of divots, holes and/or imperfections in a turf field that result from athletic and/or recreational uses (e.g., running, swinging a golf club, horse racing, etc.).

Thus, the method is also useful for enhancing the safety of a human and/or animal subject participating in athletic and recreational activities on, for example, a field or race track. In some embodiments, enhancing safety includes preventing injuries caused by, for example, stepping in a hole and/or divot. Such injuries can include, for example, broken bones, twists, sprains or strains, tripping and/or falling, and others.

In some embodiments, the method works by, for example, improving the nutrient and moisture retention properties of the rhizosphere in which the turf grass grows.

In certain embodiments, the soil treatment composition is contacted with a plant part. In a specific embodiment, the composition is contacted with one or more roots of the plant. The composition can be applied directly to the roots, e.g., by spraying or dunking the roots, and/or indirectly, e.g., by administering the composition to the soil in which the plant grows (e.g., the rhizosphere). The composition can be applied to the seeds of the plant prior to or at the time of planting, or to any other part of the plant and/or its surrounding environment.

The methods of the subject invention can utilize standard methods and equipment that are used for maintenance of turf fields. For example, the soil treatment composition can be applied in liquid form using an irrigation system. Additionally, the composition can be applied using a manual spreader, such as a broadcast spreader, a drop spreader, a handheld spreader, or a handheld sprayer.

Furthermore, the methods can be implemented on turf grasses that are already growing in soil, such as in fields and pastures, and/or the methods can be implemented on turf grasses that have been, or will be, harvested as sod.

To improve or stabilize the effects of the composition, it can be blended with suitable adjuvants and then used as such or after dilution, if necessary. In certain embodiments, the composition is formulated as a concentrated liquid preparation, or as dry powder or dry granules that can be mixed with water and other components to form a liquid product. In one embodiment, the composition comprises microbes and growth by-products, as well as the substrate in or on which the microbes were cultivated, blended together and dried to form powder or granules.

In one embodiment, the composition can comprise glucose (e.g., in the form of molasses), glycerol, glycerin, and/or other osmoticum substances, to promote osmotic pressure during storage and transport of the dry product.

DESCRIPTION OF THE FIGURES

FIG. 3 shows dry root mass measurements (g) for Ryegrass (top left), Blue Rye (top right), *Zoysia* (bottom left)

and St. Augustine (bottom right) sods, treated according to an embodiment of the subject invention, compared with standard grower's practice (untreated control).

DETAILED DESCRIPTION OF THE INVENTION

The subject invention relates to care and maintenance of turf grasses in, for example, athletics and recreational settings. More specifically, the subject invention provides methods for enhancing the health, growth and/or sturdiness of turf grass. Advantageously, the methods are low-cost, utilize non-toxic substances, and can be implemented with ease by groundskeepers with minimal additional training.

Selected Definitions

As used herein, a "biofilm" is a complex aggregate of microorganisms, wherein the cells adhere to each other and/or to surfaces. In some embodiments, the cells secrete a polysaccharide barrier that surrounds the entire aggregate. The cells in biofilms are physiologically distinct from planktonic cells of the same organism, which are single cells that can float or swim in liquid medium.

As used herein, a "biologically pure culture" is a culture that has been isolated from materials with which it exists in nature and/or in which it is produced. In a preferred embodiment, the culture has been isolated from all other materials and living cells. In further preferred embodiments, the biologically pure culture has advantageous characteristics compared to a culture of the same microbe as it exists in nature and/or in the presence of other materials. The advantageous characteristics can be, for example, enhanced production of one or more growth by-products.

As used herein, the term "control" used in reference to a pest means killing, disabling, immobilizing, or reducing population numbers of a pest, or otherwise rendering the pest substantially incapable of reproducing and/or causing harm.

As used herein, "enhancing" means improving or increasing. For example, enhanced plant health means an improved vigor and ability to thrive. Enhanced plant growth means increased size and/or biomass. Enhanced plant sturdiness includes improved ability to ward off pests and/or diseases, to withstand physical insult, such as being pulled at or tread on, and to survive environmental stressors, such as drought and/or over-watering.

As used herein, an "isolated" or "purified" compound is substantially free of other compounds, such as cellular material, with which it is associated in nature and/or in which it is produced. A purified or isolated polynucleotide (ribonucleic acid (RNA) or deoxyribonucleic acid (DNA)) is free of genes or sequences that flank it in its naturally-occurring state. A purified or isolated polypeptide is free of the amino acids or sequences that flank it in its naturally-occurring state. "Isolated" in the context of a microbial strain means that the strain is removed from the environment in which it exists in nature. Thus, the isolated strain may exist as, for example, a biologically pure culture, or as spores (or other forms of the strain).

In certain embodiments, purified compounds are at least 60% by weight the compound of interest. Preferably, the preparation is at least 75%, more preferably at least 90%, and most preferably at least 99%, by weight the compound of interest. For example, a purified compound is preferably one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis.

A "metabolite" refers to any substance produced by metabolism (e.g., a growth by-product) or a substance necessary for taking part in a particular metabolic process. Examples of metabolites include, but are not limited to, biosurfactants, biopolymers, enzymes, acids, solvents, alcohols, proteins, vitamins, minerals, microelements, and amino acids.

As used herein, "modulate" means to cause an alteration (e.g., increase or decrease).

As used herein, a "pathogenic" organism is any organism that is capable of causing a disease in another organism. Typically, pathogenic organisms are infectious agents and can include, for example, bacteria, viruses, fungi, molds, protozoa, prions, parasites, helminths, and algae.

As used herein, a "pest" is any organism, other than a human, that is destructive, deleterious and/or detrimental to humans or human concerns (e.g., agriculture, horticulture). In some, but not all instances, a pest may be a pathogenic organism. Pests may cause or be a vector for infections, infestations and/or disease, or they may simply feed on or cause other physical harm to living tissue. Pests may be single- or multi-cellular organisms, including but not limited to, viruses, fungi, bacteria, parasites, arthropods and/or nematodes.

The term "plant tissue" includes differentiated and undifferentiated tissues of plants including those present in roots, shoots, leaves, pollen, seeds and tumors, as well as cells in culture (e.g., single cells, protoplasts, embryos, callus, etc.). Plant tissue may be in planta, in organ culture, tissue culture, or cell culture. The term "plant part" as used herein refers to a plant structure or a plant tissue. Plant structures include, but are not limited to, a fruit, a seed, a shoot, a stem, a leaf, a flower petal, etc. Furthermore, the plant can be standing alone, for example, in a garden, or it can be one of many plants, for example, as part of a field or crop.

As used herein "preventing" or "prevention" of a situation or occurrence means delaying, inhibiting, suppressing, forestalling, and/or minimizing the onset, extensiveness or progression of the situation or occurrence. Prevention can include, but does not require, indefinite, absolute or complete prevention, meaning the situation or occurrence may still develop at a later time. Prevention can include reducing the severity of the onset of such a situation or occurrence, and/or inhibiting the progression thereof to one that is more severe.

Ranges provided herein are understood to be shorthand for all of the values within the range. For example, a range of 1 to 20 is understood to include any number, combination of numbers, or sub-range from the group consisting of 1, 2, 3, 4, 5, 6, 7, 8, 9, 10, 11, 12, 13, 14, 15, 16, 17, 18, 19, 20, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

As used herein, "reduce" refers to a negative alteration, and the term "increase" refers to a positive alteration, each of at least 1%, 5%, 10%, 25%, 50%, 75%, or 100%, inclusive of the values therebetween.

As used herein, "surfactant" refers to a compound that lowers the surface tension (or interfacial tension) between two liquids, between a liquid and a gas, or between a liquid and a solid. Surfactants act as, e.g., detergents, wetting agents, emulsifiers, foaming agents, and dispersants. A "biosurfactant" is a surfactant produced by a living organism.

The transitional term "comprising," which is synonymous with "including," or "containing," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention. Use of the term "comprising" contemplates other embodiments that "consist" or "consist essentially of" the recited component(s).

Unless specifically stated or obvious from context, as used herein, the term "or" is understood to be inclusive. Unless specifically stated or obvious from context, as used herein, the terms "a," "and" and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

All references cited herein are hereby incorporated by reference in their entirety.

Methods of Enhancing Plant Root Health and Immune Health

The subject invention relates to care and maintenance of turf grasses in, for example, athletics and recreational settings. More specifically, the subject invention provides materials and methods for enhancing the health, growth and sturdiness of turf grass. Advantageously, the methods are low-cost, utilize non-toxic substances, and can be implemented with ease by grounds-keeping employees with minimal additional training.

In one embodiment, the methods comprise applying a soil treatment composition comprising one or more microorganisms, growth by-products thereof, and, optionally, nutrients, to the roots of the grass and/or to the soil in which the grass grows. Advantageously, the soil treatment compositions are non-toxic and can be applied in high concentrations without causing irritation to, for example, the skin or digestive tract of a human or other non-pest animal. Thus, the subject invention is particularly useful where application of the soil treatment compositions occurs in the presence of living organisms, such as groundskeepers and/or athletes.

In certain embodiments, the soil treatment composition is, or comprises, a "microbe-based composition," meaning a composition that comprises components that were produced as the result of the growth of microorganisms or other cell cultures. A microbe-based composition may comprise the microbes themselves and/or by-products of microbial growth. The microbes may be in a vegetative state, in spore or conidia form, in hyphae form, in any other form of propagule, or a mixture of these. The microbes may be planktonic or in a biofilm form, or a mixture of both. The by-products of growth may be, for example, metabolites, cell membrane components, expressed proteins, and/or other cellular components. The microbes may be intact or lysed. In preferred embodiments, the microbes are present, with growth medium in which they were grown, in the microbe-based composition. The microbes may be present at, for example, a concentration of at least $1\times10^4$, $1\times10^5$, $1\times10^6$, $1\times10^7$, $1\times10^8$, $1\times10^9$, $1\times10^{10}$, $1\times10^{11}$, $1\times10^{12}$ or $1\times10^{13}$ or more CFU per gram or per ml of the composition. In one embodiment, the microorganisms of the subject composition comprise about 5 to 20% of the total composition by weight, or about 8 to 15%, or about 10 to 12%.

The microorganisms useful according to the subject invention can be, for example, non-plant-pathogenic strains of bacteria, yeast and/or fungi. These microorganisms may be natural, or genetically modified microorganisms. For example, the microorganisms may be transformed with specific genes to exhibit specific characteristics. The microorganisms may also be mutants of a desired strain. As used herein, "mutant" means a strain, genetic variant or subtype of a reference microorganism, wherein the mutant has one or more genetic variations (e.g., a point mutation, missense mutation, nonsense mutation, deletion, duplication, frameshift mutation or repeat expansion) as compared to the reference microorganism. Procedures for making mutants are well known in the microbiological art. For example, UV mutagenesis and nitrosoguanidine are used extensively toward this end.

In one embodiment, the composition comprises a yeast or fungus. Yeast and fungus species suitable for use according to the current invention, include *Aureobasidium* (e.g., *A. pullulans*), *Blakeslea*, *Candida* (e.g., *C. apicola, C. bombicola, C. nodaensis*), *Cryptococcus*, *Debaryomyces* (e.g., *D. hansenii*), *Entomophthora*, *Hanseniaspora*, (e.g., *H. uvarum*), *Hansenula*, *Issatchenkia*, *Kluyveromyces* (e.g., *K. phaffii*), *Mortierella*, mycorrhizal fungi, *Penicillium*, *Phycomyces*, *Pichia* (e.g., *P. anomala, P. guilliermondii, P. occidentalis, P. kudriavzevii*), *Pleurotus* spp. (e.g., *P. ostreatus*), *Pseudozyma* (e.g., *P. aphidis*), *Saccharomyces* (e.g., *S. boulardii sequela, S. cerevisiae, S. torula*), *Starmerella* (e.g., *S. bombicola*), *Torulopsis*, *Trichoderma* (e.g., *T. reesei, T. harzianum, T. hamatum, T. viride*), *Ustilago* (e.g., *U. maydis*), *Wickerhamomyces* (e.g., *W. anomalus*), *Williopsis* (e.g., *W. mrakii*), *Zygosaccharomyces* (e.g., *Z. bailii*), and others.

In certain embodiments, the microorganisms are bacteria, including Gram-positive and Gram-negative bacteria. The bacteria may be, for example *Agrobacterium* (e.g., *A. radiobacter*), *Azotobacter* (*A. vinelandii, A. chroococcum*), *Azospirillum* (e.g., *A. brasiliensis*), *Bacillus* (e.g., *B. amyloliquifaciens, B. circulans, B. firmus, B. laterosporus, B. licheniformis, B. megaterium, Bacillus mucilaginosus, B. subtilis*), *Frateuria* (e.g., *F. aurantia*), *Microbacterium* (e.g.,

*M. laevaniformans*), myxobacteria (e.g., *Myxococcus xanthus, Stignatella aurantiaca, Sorangium cellulosum, Minicystis rosea*), *Pantoea* (e.g., *P. agglomerans*), *Pseudomonas* (e.g., *P. aeruginosa, P. chlororaphis* subsp. *aureofaciens* (*Kluyver*), *P. putida*), *Rhizobium* spp., *Rhodospirillum* (e.g., *R. rubrum*), *Sphingomonas* (e.g., *S. paucimobilis*), and/or *Thiobacillus thiooxidans* (*Acidothiobacillus thiooxidans*).

In certain embodiments, the soil treatment composition comprises one or more of these microorganisms, growth by-products thereof, and, optionally, one or more sources of nutrients. In certain embodiments, the microorganisms of the composition work synergistically with one another to enhance health, growth and/or yields in plants.

In a specific exemplary embodiment, the soil treatment composition comprises a first microorganism, which is preferably a conidia-forming (spore-forming) fungal strain, and a second microorganism, which is preferably a spore-forming bacterial strain. Preferably, the first microorganism is a *Trichoderma* spp. fungus and the second microorganism is a spore-forming *Bacillus* spp. bacterium, although other combinations are envisioned. In certain embodiments, the composition comprises *Trichoderma harzianum* and *Bacillus amyloliquefaciens*. In some embodiments, the *Bacillus* microbe can solubilize phosphorus compounds in the soil. In a specific embodiment, the *Bacillus* is *B. amyloliquefaciens* is *B. amyloliquefaciens* NRRL B-67928.

Certain species of *Trichoderma* are useful when added to soil, where they can multiply and grow in close association with plants' roots. They are capable of partially protecting the roots from invasion by other plant pathogenic fungi and other microbial and animal pests, in addition to helping to stimulate plant growth.

*Trichoderma* can establish strong and long-lasting colonization of root surfaces, penetrating into the epidermis and shallow subsurface cells. These root-microorganism associations cause substantial changes to the plant proteome and metabolism. They produce and/or release a variety of compounds that induce localized or systemic resistance responses, causing a lack of pathogenicity to plants.

Additionally, plants are protected from numerous classes of plant pathogen by responses that are similar to systemic acquired resistance and rhizobacteria-induced systemic resistance. *Trichoderma* spp. can effectively reduce diseases caused by some soil-borne plant pathogens. For example, the species *T. harzianum, T. hamatum,* and *T. viride* have fungicidal activity against *Sclerotium, Rhizoctonia, Solani, Pythium, Fusarium, Cercospora, Ralstonia, Fragaria, Rhizopus, Botrytis, Colletotrichum, Magnaporthe*, and many others. Moreover, some strains of *Trichoderma* are able to effectively suppress the growth of some viral and bacterial plant and soil pathogens, as well as produce some significant nematocidal effects.

In addition to protecting plants from pathogens and pests, root colonization by *Trichoderma* spp. can enhance root growth and development, crop productivity, resistance to abiotic stresses, and bioavailability of nutrients.

A culture of the *B. amyloliquefaciens* "B. amy" microbe has been deposited with the Agricultural Research Service Northern Regional Research Laboratory (NRRL), Culture Collection, 1815 N. University St., Peoria, IL, USA446 USA. The deposit has been assigned accession number NRRL B-67928 by the depository. The deposit was deposited on Feb. 26, 2020 and deemed viable by the depository on Mar. 3, 2020.

The subject culture has been deposited under conditions that assure that access to the culture will be available during the pendency of this patent application to one determined by the Commissioner of Patents and Trademarks to be entitled thereto under 37 CFR 1.14 and 35 U.S.C 122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least 30 (thirty) years after the date of deposit or for the enforceable life of any patent which may issue disclosing the culture. The depositor acknowledges the duty to replace the deposit should the depository be unable to furnish a sample when requested, due to the condition of the deposit. The deposit *B. amyloliquefaciens* NRRL B-67928 is viable, commercially available, reproducible, and all restrictions on the availability to the public of the subject culture deposit will be irrevocably removed upon the granting of a patent disclosing it.

In one embodiment, the composition can comprise from 1 to 99% *T. harziaum* culture by volume and from 99 to 1% *B. amy* culture by volume. In some embodiments, the cell count ratio of *T. harzianum* to *B. amy* is about 1:9 to about 9:1, about 1:8 to about 8:1, about 1:7 to about 7:1, about 1:6 to about 6:1, about 1:5 to about 5:1 or about 1:4 to about 4:1.

In one embodiment, the composition comprises about $1 \times 10^6$ to $1 \times 10^{12}$, $1 \times 10^7$ to $1 \times 10^{11}$, $1 \times 10^8$ to $1 \times 10^{10}$, or $1 \times 10^9$ CFU/ml of *Trichoderma*. In one specific embodiment, the composition comprises about $1 \times 10^6$ to $1 \times 10^{12}$, $1 \times 10^7$ to $1 \times 10^{11}$, $1 \times 10^8$ to $1 \times 10^{10}$, or $1 \times 10^9$ CFU/ml of *Bacillus*.

In some embodiments, the composition can comprise a mycobacterium, or slime-forming bacteria. Specifically, in one embodiment, the mycobacterium is a *Myxococcus* spp. bacterium, e.g., *M. xanthus*.

In some embodiments, the composition can comprise a microorganism that is capable of fixing and/or solubilizing nitrogen, potassium, phosphorous and/or other micronutrients in soil.

In one embodiment, the composition can comprise a nitrogen-fixing microorganism, or a diazotroph, selected from species of, for example, *Azospirillum, Azotobacter, Chlorobiaceae, Cyanothece, Frankia, Klebsiella, rhizobia, Trichodesmium*, and some *Archaea*. In a specific embodiment, the nitrogen-fixing microorganism is *Azotobacter vinelandii*.

In one embodiment, the composition can comprise a potassium-mobilizing microorganism, or KMB, selected from, for example, *Bacillus mucilaginosus, Frateuria aurantia* and *Glomus mosseae*. In a specific embodiment, the potassium-mobilizing microorganism is *Frateuria aurantia*.

In one embodiment, the composition can comprise one or more of *Pseudomonas chlororaphis, Wickerhamomyces anomalus, Starmerella bombicola, Saccharomyces boulardii, Pichia occidentalis, Pichia kudriavzevii,* and/or *Meyerozyma guilliermondii*.

In one embodiment, the composition can comprise a mycorrhizal fungus. As used herein, "mycorrhizal fungi" includes any species of fungus that forms a non-parasitic mycorrhizal relationship with a plant's roots. The fungi can be ectomycorrhizal fungi and/or endomycorrhizal fungi, including subtypes thereof (e.g., arbuscular, ericoid, and orchid mycorrhizae).

Non-limiting examples of mycorrhizal fungi according to the subject invention include species belong to Glomeromycota, Basidiomycota, Ascomycota, Zygomycota, Helotiales, and Hymenochaetales, as well as *Acaulospora* spp. (e.g., *A. alpina, A. brasiliensis, A. foveata*), *Amanita* spp. (e.g., *A. muscaria, A. phalloides*), *Amphinema* spp. (e.g., *A. byssoides, A. diadema, A. rugosum*), *Astraeus* spp. (e.g., *A. hygrometricum*), *Byssocorticium* spp. (e.g., *B. atrovirens*), *Byssoporia terrestris* (e.g., *B. terrestris sartoryi, B. terrestris lilacinorosea, B. terrestris aurantiaca, B. terrestris sublutea, B. terrestris parksii*), *Cairneyella* spp. (e.g., *C. variabilis*), *Cantherellus* spp. (e.g., *C. cibarius, C. minor, C. cinnabarinus, C. friesii*), *Cenococcum* spp. (e.g., *C. geophilum*), *Ceratobasidium* spp. (e.g., *C. cornigerum*), *Cortinarius* spp. (e.g., *C. austrovenetus, C. caperatus, C. violaceus*), *Endogone* spp. (e.g., *E. pisiformis*), *Entrophospora* spp. (e.g., *E. colombiana*), *Funneliformis* spp. (e.g., *F. mosseae*), *Gamarada* spp. (e.g., *G. debralockiae*), *Gigaspora* spp. (e.g., *G. gigantean, G. margarita*), *Glomus* spp. (e.g., *G. aggregatum, G. brasilianum, G. clarum, G. deserticola, G. etunicatum, G. fasciculatum G. intraradices, G. lamellosum, G. macrocarpum, G. monosporum, G. mosseae, G. versiforme*), *Gomphidius* spp. (e.g., *G. glutinosus*), *Hebeloma* spp. (e.g., *H. cylindrosporum*), *Hydnum* spp. (e.g., *H. repandum*), *Hymenoscyphus* spp. (e.g., *H. ericae*), *Inocybe* spp. (e.g., *I. bongardii, I. sindonia*), *Lactarius* spp. (e.g., *L. hygrophoroides*), *Lindtneria* spp. (e.g., *L. brevispora*), *Melanogaster* spp. (e.g., *M. ambiguous*), *Meliniomyces* spp. (e.g., *M variabilis*), *Morchella* spp., *Mortierella* spp. (e.g., *M. polycephala*), *Oidiodendron* spp. (e.g., *O. maius*), *Paraglomus* spp. (e.g., *P. brasilianum*), *Paxillus* spp. (e.g., *P. involutus*), *Penicillium* spp. (e.g., *P. pinophilum, P. thomili*), *Peziza* spp. (e.g., *P. whitei*), *Pezoloma* spp. (e.g., *P. ericae*); *Phlebopus* spp. (e.g., *P. marginatus*), *Piloderma* spp. (e.g., *P. croceum*), *Pisolithus* spp. (e.g., *P. tinctorius*), *Pseudotomentella* spp. (e.g., *P. tristis*), *Rhizoctonia* spp., *Rhizodermea* spp. (e.g., *R. veluwensis*), *Rhizophagus* spp. (e.g., *R. irregularis*), *Rhizopogon* spp. (e.g., *R. luteorubescens, R. pseudoroseolus*), *Rhizoscyphus* spp. (e.g., *R. ericae*), *Russula* spp. (e.g., *R. livescens*), *Sclerocystis* spp. (e.g., *S. sinuosum*), *Scleroderma* spp. (e.g., *S. cepa, S. verrucosum*), *Scutellospora* spp. (e.g., *S. pellucida, S. heterogama*), *Sebacina* spp. (e.g., *S. sparassoidea*), *Setchelliogaster* spp. (e.g., *S. tenuipes*), *Suillus* spp. (e.g., *S. luteus*), *Thanatephorus* spp. (e.g., *T cucumeris*), *Thelephora* spp. (e.g., *T. terrestris*), *Tomentella* spp. (e.g., *T. badia, T. cinereoumbrina, T. erinalis, T. galzinii*), *Tomentellopsis* spp. (e.g., *T. echinospora*), *Trechispora* spp. (e.g., *T. hymenocystis, T. stellulata, T. thelephora*), *Trichophaea* spp. (e.g., *T. abundans, T. woolhopeia*), *Tulasnella* spp. (e.g., *T. calospora*), and *Tylospora* spp. (e.g., *T. fibrillose*).

In certain preferred embodiments, the subject invention utilizes endomycorrhizal fungi, including fungi from the phylum Glomeromycota and the genera *Glomus, Gigaspora, Acaulospora, Sclerocystis,* and *Entrophospora*. Examples of endomycorrhizal fungi include, but are not limited to, *Glomus aggregatum, Glomus brasilianum, Glomus clarum, Glomus deserticola, Glomus etunicatum, Glomus fasciculatum, Glomus intraradices (Rhizophagus irregularis), Glomus lamellosum, Glomus macrocarpum, Gigaspora margarita, Glomus monosporum, Glomus mosseae (Funneliformis mosseae), Glomus versiforme, Scutellospora heterogama,* and *Sclerocystis* spp.

In a specific embodiment, microbes are included at a concentration of $1\times10^8$ to $1\times10^{11}$, or $1\times10^9$ to $1\times10^{10}$ CFU/ml each.

The species and ratio of microorganisms and other ingredients in the composition can be determined according to, for example, the species of grass being treated, the soil type where the turf is growing, the health of the turf at the time of treatment, as well as other factors. Thus, the composition can be customizable for any given turf field. Advantageously, in some embodiments, the combination of microbes works synergistically with one another to enhance plant health, growth and/or yields.

In a specific exemplary embodiment, the composition comprises *T. harzianum, B. amyloliquefaciens* NRRL B-67928 and, optionally, one or more additional microorganisms described above.

In a specific exemplary embodiment, the composition comprises *T harzianum, B. amyloliquefaciens* NRRL B-67928, a mycorrhizal fungus and, optionally, one or more additional microorganisms described above.

In a specific exemplary embodiment, the composition comprises *Wickerhamomyces anomalus* and, optionally, one or more additional microorganisms described above.

In a specific exemplary embodiment, the composition comprises *Wickerhamomyces anomalus*, a mycorrhizal fungus and, optionally, one or more additional microorganisms described above.

In one embodiment, the soil treatment composition further comprises microbial growth by-products, which can include, for example, the fermentation medium in which the microbes were cultivated, and/or any residual nutrients from cultivation.

The growth by-products can also include metabolites or other biochemicals produced as a result of cell growth, including, for example, biosurfactants, enzymes and/or solvents.

In one embodiment, the microorganisms of the subject composition are capable of producing a biosurfactant. In another embodiment, biosurfactants can be produced separately by other microorganisms and added to the composition, either in purified form or in crude form. Crude form biosurfactants can comprise, for example, biosurfactants and other products of cellular growth in the leftover fermentation medium resulting from cultivation of a biosurfactant-producing microbe. This crude form biosurfactant composition can comprise from about 0.001% to about 90%, about 25% to about 75%, about 30% to about 70%, about 35% to about 65%, about 40% to about 60%, about 45% to about 55%, or about 50% pure biosurfactant.

Biosurfactants form an important class of secondary metabolites produced by a variety of microorganisms such as bacteria, fungi, and yeasts. As amphiphilic molecules, microbial biosurfactants reduce the surface and interfacial tensions between the molecules of liquids, solids, and gases. Furthermore, the biosurfactants according to the subject invention are biodegradable, have low toxicity, are effective in solubilizing and degrading insoluble compounds in soil and can be produced using low cost and renewable resources. They can inhibit adhesion of undesirable microorganisms to a variety of surfaces, prevent the formation of biofilms, and can have powerful emulsifying and demulsifying properties. Furthermore, the biosurfactants can also be used to improve wettability and to achieve even solubilization and/or distribution of fertilizers, nutrients, and water in the soil.

Biosurfactants according to the subject methods can be selected from, for example, low molecular weight glycolipids (e.g., sophorolipids, cellobiose lipids, rhamnolipids, mannosylerythritol lipids and trehalose lipids), lipopeptides (e.g., surfactin, iturin, fengycin, arthrofactin and lichenysin), flavolipids, phospholipids (e.g., cardiolipins), and high molecular weight polymers such as lipoproteins, lipopolysaccharide-protein complexes, and polysaccharide-protein-fatty acid complexes.

The composition can comprise one or more biosurfactants at a concentration of 0.001% to 10%, 0.01% to 5%, 0.05% to 2%, and/or from 0.1% to 1%.

Advantageously, in accordance with the subject invention, the soil treatment composition may comprise the medium in which each microorganism was grown. The composition may be, for example, at least, by weight, 1%, 5%, 10%, 25%, 50%, 75%, or 100% growth medium.

The fermentation medium can contain a live and/or an inactive culture, purified or crude form growth by-products, such as biosurfactants, enzymes, and/or other metabolites, and/or any residual nutrients. The amount of biomass in the composition, by weight, may be, for example, anywhere from about 0.01% to 100%, about 1% to 90%, about 5% to about 80%, or about 10% to about 75%.

The product of fermentation may be used directly, with or without extraction or purification. If desired, extraction and purification can be easily achieved using standard extraction and/or purification methods or techniques described in the literature.

The microorganisms in the soil treatment composition may be in an active or inactive form, or in the form of vegetative cells, reproductive spores, mycelia, hyphae, conidia or any other form of microbial propagule. The composition may also contain a combination of any of these microbial forms.

In one embodiment, different species of microorganism are grown separately and then mixed together to produce the soil treatment composition. In one embodiment, microorganisms can be co-cultivated, for example, *B. amyloliquefaciens* and *M. xanthus*.

The methods can further comprise applying materials to enhance microbe growth during application (e.g., adding nutrients to promote microbial growth). In one embodiment, the nutrient sources can include, for example, sources of magnesium, phosphate, nitrogen, potassium, selenium, calcium, sulfur, iron, copper, zinc, proteins, vitamins and/or carbon.

In one embodiment, the method further comprises applying one or more prebiotics with the soil treatment composition. For example, suitable prebiotics can include one or more of kelp extract, fulvic acid, chitin, humate and humic acid.

In some embodiments, the method further comprises applying additional components, such as herbicides, fertilizers, pesticides and/or soil amendments. Preferably, the additional components are non-toxic and environmentally-friendly. The exact materials and the quantities thereof can be determined by a groundskeeper or an turf scientist having the benefit of the subject disclosure, although the following provide compounds that are compatible with the subject methods:

In one embodiment, the subject compositions are compatible for use with agricultural compounds characterized as antiscalants, such as, e.g., hydroxyethylidene diphosphonic acid;

bactericides, such as, e.g., streptomycin sulfate and/or Galltrol® (*A. radiobacter* strain K84);

biocides, such as, e.g., chlorine dioxide, didecyldimethyl ammonium chloride, halogenated heterocyclic, and/or hydrogen dioxide/peroxyacetic acid;

fertilizers, such as, e.g., N-P-K fertilizers, calcium ammonium nitrate 17-0-0, potassium thiosulfate, nitrogen (e.g., 10-34-0, Kugler KQ-XRN, Kugler KS-178C, Kugler KS-2075, Kugler LS 6-24-6S, UN 28, UN 32), and/or potassium;

fungicides, such as, e.g., chlorothalonil, manicozeb hexamethylenetetramine, aluminum tris, azoxystrobin, *Bacillus* spp. (e.g., *B. licheniformis* strain 3086, *B. subtilis*, *B. subtilis* strain QST 713), benomyl, boscalid, pyraclostrobin, captan, carboxin, chloroneb, chlorothalonil, copper culfate, cyazofamid, dicloran, dimethomorph, etridiazole, thiophanate-methyl, fenamidone, fenarimol, fludioxonil, fluopicolide, flutolanil, iprodione, mancozeb, maneb, mefanoxam, fludioxonil, mefenoxam, metalaxyl, myclobutanil, oxathiapiprolin, pentachloronitrobenzene (quintozene), phosphorus acid, propamocarb, propanil, pyraclostrobin, *Reynoutria sachalinensis*, *Streptomyces* spp. (e.g., *S. griseoviridis* strain K61, *S. lydicus* WYEC 108), sulfur, urea, thiabendazole, thiophanate methyl, thiram, triadimefon, triadimenol, and/or vinclozolin;

growth regulators, such as, e.g., ancymidol, chlormequat chloride, diaminozide, paclobutrazol, and/or uniconazole;

herbicides, such as, e.g., glyphosate, oxyfluorfen, and/or pendimethalin;

insecticides, such as, e.g., acephate, azadirachtin, *B. thuringiensis* (e.g., subsp. *israelensis* strain AM 65-52), *Beauveria bassiana* (e.g., strain GHA), carbaryl, chlorpyrifos, cyantraniliprole, cyromazine, dicofol, diazinon, dinotefuran, imidacloprid, *Isaria fumosorosae* (e.g., Apopka strain 97), lindane, and/or malathion;

water treatments, such as, e.g., hydrogen peroxide (30-35%), phosphonic acid (5-20%), and/or sodium chlorite;

as well as glycolipids, lipopeptides, deet, diatomaceous earth, citronella, essential oils, mineral oils, garlic extract, chili extract, and/or any known commercial and/or homemade pesticide that is determined to be compatible by the skilled artisan having the benefit of the subject disclosure.

Preferably, the method is not employed simultaneously with, or within 7 to 10 days before or after, application of the following compounds: benomyl, dodecyl dimethyl ammonium chloride, hydrogen dioxide/peroxyacetic acid, imazilil, propiconazole, tebuconazole, or triflumizole.

As used herein, "applying" a composition or product refers to contacting a composition or product with a target or site such that the composition or product can have an effect on that target or site. The effect can be due to, for example, microbial growth and/or the action of a metabolite, enzyme, biosurfactant, or other growth by-product.

In certain embodiments, the soil treatment composition is contacted with a plant part. In a specific embodiment, the composition is contacted with one or more roots of the plant. The composition can be applied directly to the roots, e.g., by spraying or dunking the roots, and/or indirectly, e.g., by administering the composition to the soil in which the plant grows (e.g., the rhizosphere). It can be sprayed, poured, sprinkled, injected or spread as liquid, dry powder, dust, granules, microgranules, pellets, wettable powder, flowable powder, emulsions, microcapsules, oils, gels, pastes or aerosols. Furthermore, the composition can be applied to the seeds of the plant prior to or at the time of planting, or to any other part of the plant and/or its surrounding environment.

Plants and/or their environments can be treated at any point during the process of cultivating the plant. For example, the soil treatment composition can be applied to the soil prior to, concurrently with, or after the time when seeds are planted therein. It can also be applied at any point thereafter during the development and growth of the plant, including when the plant is flowering or fruiting.

In some embodiments, the methods can be implemented on turf grasses that are already planted and growing in soil, such as in fields, pitches and pastures, and/or the methods can be implemented on turf grasses that have been, or will be, harvested as sod.

To improve or stabilize the effects of the composition, it can be blended with suitable adjuvants and then used as such or after dilution, if necessary. In certain embodiments, the composition is formulated as a concentrated liquid preparation, or as dry powder or dry granules that can be mixed with water and other components to form a liquid product. In one embodiment, the composition comprises the substrate, microbes and growth by-products, blended together and dried to form powder or granules.

In one embodiment, the composition can comprise glucose (e.g., in the form of molasses), glycerol and/or glycerin, as, or in addition to, an osmoticum substance, to promote osmotic pressure during storage and transport of the dry product.

The methods of the subject invention can utilize standard equipment that is used for maintenance of turf fields. In one embodiment, the method can comprise administering the composition into a tank connected to an irrigation system used for supplying water, fertilizers, pesticides or other liquid compositions to a field. Thus, the plant and/or soil surrounding the plant can be treated with the composition via, for example, soil injection, soil drenching, or using a center pivot irrigation system, or with a spray over the seed furrow, or with sprinklers or drip irrigators. Advantageously, the method is suitable for treating hundreds of acres at one time.

In one embodiment, the method can comprise pouring the soil treatment composition into the tank of a handheld lawn and garden sprayer and spraying a plant and/or its surrounding environment with the mixture. The composition can also be mixed into a standard handheld watering can and poured onto soil. Additionally, the composition can be applied using a standard manual spreader, such as a broadcast spreader, a drop spreader, or a handheld spreader.

In certain embodiments, the compositions provided herein are applied to the soil surface without mechanical incorporation. The beneficial effect of the soil application can be activated by rainfall, sprinkler, flood, or drip irrigation, and subsequently delivered to, for example, the roots of plants to influence the root microbiome and/or facilitate uptake of nutrients and water.

In one embodiment, the method enhances the health, growth and sturdiness of turf grass by enhancing the strength of the root system. In certain embodiments, enhanced root strength comprises increased tensile strength of a root or root system, meaning increased ability to resist breaking under tension. In certain embodiments, enhanced root strength comprises increased tensile strength of a sheet of sod. Root strength can be enhanced by, for example, increasing root numbers and/or density, as well as increasing the diameter and rooting depth of individual roots.

Figure 1A:
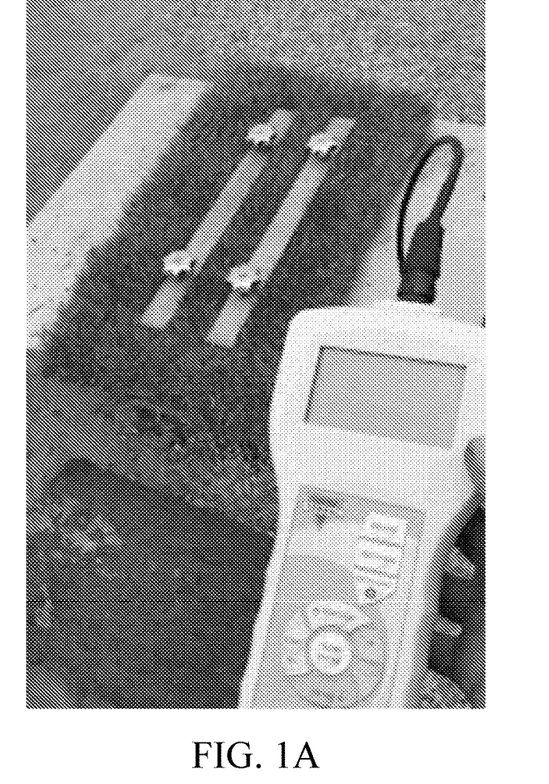
FIGS. 1A-1B show a device used for measuring tensile strength of a sheet of sod. (1A) shows a sheet of sod with teethed mounts attached, as well as a force meter to measure the tensile force applied to the sod. (1B) shows a device before the sheet of sod in (1A) has been loaded. The teethed mounts with sod are loaded in parallel onto the four rods protruding from the top of the device. The two white arrows show the direction in which the tensile strength is applied to the loaded sod.
Figure 1B:
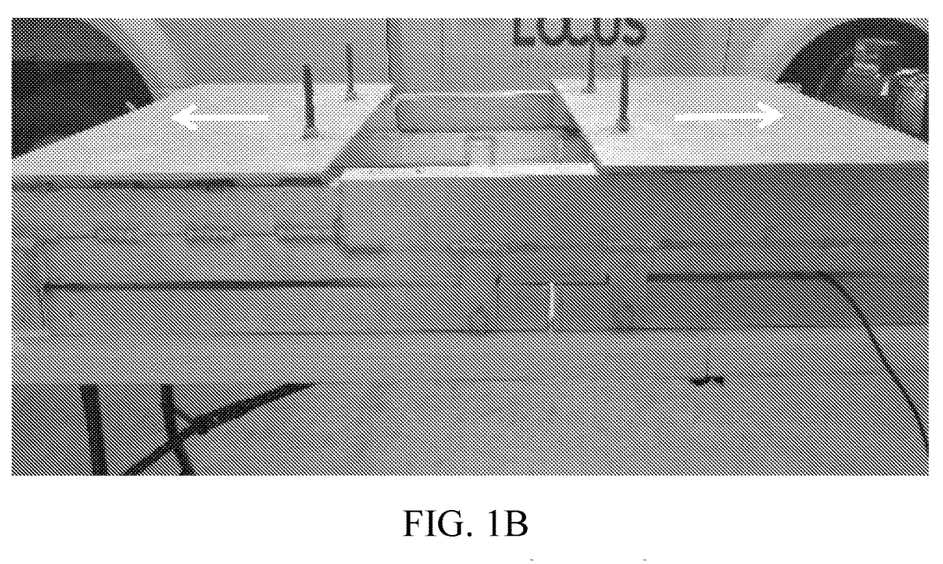

In certain embodiments, the methods of the subject invention further comprise testing the grass for root tensile strength after treatment with the soil treatment composition. Testing can include, for example, using a tensile testing machine with a force meter to determine tensile strength of individual roots and/or root systems, and/or testing for the tensile breaking force required to tear a sheet of sod apart. FIGS. 1A-1B.

In one embodiment, by enhancing root strength, the methods improve the ability of the grass plants to remain anchored in soil without being uplifted or carved out due to the activities being conducted thereon. For example, the methods can be used to reduce the number of divots, holes and/or imperfections in a turf field that result from athletic and/or recreational uses (e.g., running, kicking a ball, swinging a golf club or hockey stick, horse racing, etc.).

Thus, the method is also useful for enhancing the safety of participating in athletic and recreational activities on a field by preventing injuries caused by stepping in a hole and/or divot, such as, for example, twisted ankles or tripping.

In some embodiments, the method works by, for example, improving the nutrient and moisture retention properties of the rhizosphere in which the turf grass grows. In some embodiments, the method works by promoting colonization of the roots and/or rhizosphere with nutrient-fixing microbes, such as *rhizobia* and mycorrhizae.

In one embodiment, the method can be used for enhancing penetration of beneficial molecules through the outer layers of root cells.

The subject invention can be used to improve any number of qualities in any type of soil, for example, clay, sandy, silty, peaty, chalky, loam soil, and/or combinations thereof. Furthermore, the methods and compositions can be used for improving the quality of dry, waterlogged, porous, depleted, compacted soils and/or combinations thereof.

In one embodiment, the method can be used for improving the drainage and/or dispersal of water in waterlogged soils. In one embodiment, the method can be used for improving water retention in dry soil. In one embodiment, the method can be used for improving nutrient retention in porous and/or depleted soils.

The methods of the subject invention can be used to enhance the health, growth and sturdiness of any species of turf grass. These include, include, but are not limited to: annual bluegrass (*Poa annua*); annual ryegrass (*Lolium multiflorum*); Canada bluegrass (*Poa compressa*); Chewings fescue (*Festuca rubra*); colonial bentgrass (*Agrostis tenius*); creeping bentgrass (*Agrostis palustris*); crested wheatgrass (*Agropyron desertorum*); fairway wheatgrass (*Agropyron cristatum*); hard fescue (*Festuca longifolia*); Kentucky bluegrass (*Poa pratensis*); orchardgrass (*Dactylis glomerate*); perennial ryegrass (*Lolium perenne*); red fescue (*Festuca rubra*); redtop (*Agrostis alba*); rough bluegrass (*Poa trivialis*); sheep fescue (*Festuca ovine*); smooth bromegrass (*Bromus inermis*); tall fescue (*Festuca arundinacea*); timothy (*Phleum pretense*); velvet bentgrass (*Agrostis canine*); weeping alkaligrass (*Puccinellia distans*); western wheatgrass (*Agropyron smithii*); Bermuda grass (*Cynodon* spp.); St. Augustine grass (*Stenotaphrum secundatum*); zoysia grass (*Zoysia* spp.); Bahia grass (*Paspalum notatum*); carpet grass (*Axonopus affinis*); centipede grass (*Eremochloa ophiuroides*); kikuyu grass (*Pennisetum clandesinum*); seashore paspalum (*Paspalum vaginatum*); floratam (*Stenotaphrum secundatum* "Floratam"); blue gramma (*Bouteloua gracilis*); buffalo grass (*Buchloe dactyloids*); sideoats gramma (*Bouteloua curtipendula*).

In some embodiments, the turf grass is in the form of sod. As used herein, "sod" means sheets of turf grass comprising grass plants, their roots, and any soil that is attached thereto. The sheets can be harvested and transplanted to cover large surface areas of ground.

In some embodiments, the turf grass is growing in a field, or expanse of open ground, used for athletics and/or recreation. "Recreation," as used herein, comprises activities that are done for enjoyment, leisure, and/or pleasure, such as, for example, playing games (e.g., tag, catch, Frisbee), camping, attending festivals or concerts, and horseback riding.

The field can be located at, for example, a park, a dog park, a playground, a stadium, a yard, a school, a church, a recreation center, a campground, an outdoor amphitheater, or any other venue used for athletics and/or recreation.

The field can be an athletic field or pitch, such as, for example, a golf course, disc golf course, horse track, soccer field, football field, lacrosse field, field hockey field, cricket field, rugby field, polo field, softball field, baseball field, tennis court, volleyball court, backgammon court, badminton court, and/or track and field stadium.

Growth of Microbes According to the Subject Invention

The subject invention utilizes methods for cultivation of microorganisms and production of microbial metabolites and/or other by-products of microbial growth. The subject invention further utilizes cultivation processes that are suitable for cultivation of microorganisms and production of microbial metabolites on a desired scale. These cultivation processes include, but are not limited to, submerged cultivation/fermentation, solid state fermentation (SSF), and modifications, hybrids and/or combinations thereof.

As used herein "fermentation" refers to cultivation or growth of cells under controlled conditions. The growth could be aerobic or anaerobic. In preferred embodiments, the microorganisms are grown using SSF and/or modified versions thereof.

In one embodiment, the subject invention provides materials and methods for the production of biomass (e.g., viable cellular material), extracellular metabolites (e.g. small molecules and excreted proteins), residual nutrients and/or intracellular components (e.g. enzymes and other proteins).

The microbe growth vessel used according to the subject invention can be any fermenter or cultivation reactor for industrial use. In one embodiment, the vessel may have functional controls/sensors or may be connected to functional controls/sensors to measure important factors in the cultivation process, such as pH, oxygen, pressure, temperature, humidity, microbial density and/or metabolite concentration.

In a further embodiment, the vessel may also be able to monitor the growth of microorganisms inside the vessel (e.g., measurement of cell number and growth phases).

Alternatively, a daily sample may be taken from the vessel and subjected to enumeration by techniques known in the art, such as dilution plating technique. Dilution plating is a simple technique used to estimate the number of organisms in a sample. The technique can also provide an index by which different environments or treatments can be compared.

In one embodiment, the method includes supplementing the cultivation with a nitrogen source. The nitrogen source can be, for example, potassium nitrate, ammonium nitrate, ammonium sulfate, ammonium phosphate, ammonia, urea, and/or ammonium chloride. These nitrogen sources may be used independently or in a combination of two or more.

The method can provide oxygenation to the growing culture. One embodiment utilizes slow motion of air to remove low-oxygen containing air and introduce oxygenated air. In the case of submerged fermentation, the oxygenated air may be ambient air supplemented daily through mechanisms including impellers for mechanical agitation of liquid, and air spargers for supplying bubbles of gas to liquid for dissolution of oxygen into the liquid.

The method can further comprise supplementing the cultivation with a carbon source. The carbon source is typically a carbohydrate, such as glucose, sucrose, lactose, fructose, trehalose, mannose, mannitol, and/or maltose; organic acids such as acetic acid, fumaric acid, citric acid, propionic acid, malic acid, malonic acid, and/or pyruvic acid; alcohols such as ethanol, propanol, butanol, pentanol, hexanol, isobutanol, and/or glycerol; fats and oils such as soybean oil, canola oil, rice bran oil, olive oil, corn oil, sesame oil, and/or linseed oil; etc. These carbon sources may be used independently or in a combination of two or more.

In one embodiment, growth factors and trace nutrients for microorganisms are included in the medium. This is particularly preferred when growing microbes that are incapable of producing all of the vitamins they require. Inorganic nutrients, including trace elements such as iron, zinc, copper, manganese, molybdenum and/or cobalt may also be included in the medium. Furthermore, sources of vitamins, essential amino acids, and microelements can be included, for example, in the form of flours or meals, such as corn flour, or in the form of extracts, such as yeast extract, potato extract, beef extract, soybean extract, banana peel extract, and the like, or in purified forms. Amino acids such as, for example, those useful for biosynthesis of proteins, can also be included.

In one embodiment, inorganic salts may also be included. Usable inorganic salts can be potassium dihydrogen phosphate, dipotassium hydrogen phosphate, disodium hydrogen phosphate, magnesium sulfate, magnesium chloride, iron sulfate, iron chloride, manganese sulfate, manganese chloride, zinc sulfate, lead chloride, copper sulfate, calcium chloride, sodium chloride, calcium carbonate, and/or sodium carbonate. These inorganic salts may be used independently or in a combination of two or more.

In some embodiments, the method for cultivation may further comprise adding additional acids and/or antimicrobials in the medium before, and/or during the cultivation process. Antimicrobial agents or antibiotics are used for protecting the culture against contamination.

The pH of the mixture should be suitable for the microorganism of interest. Buffers, and pH regulators, such as carbonates and phosphates, may be used to stabilize pH near a preferred value. When metal ions are present in high concentrations, use of a chelating agent in the medium may be necessary.

The microbes can be grown in planktonic form or as biofilm. In the case of biofilm, the vessel may have within it a substrate upon which the microbes can be grown in a biofilm state. The system may also have, for example, the capacity to apply stimuli (such as shear stress) that encourages and/or improves the biofilm growth characteristics.

In one embodiment, the method for cultivation of microorganisms is carried out at about 5° to about 100° C., preferably, 15 to 60° C., more preferably, 25 to 50° C. In a further embodiment, the cultivation may be carried out continuously at a constant temperature. In another embodiment, the cultivation may be subject to changing temperatures.

In one embodiment, the equipment used in the method and cultivation process is sterile. The cultivation equipment such as the reactor/vessel may be separated from, but connected to, a sterilizing unit, e.g., an autoclave. The cultivation equipment may also have a sterilizing unit that sterilizes in situ before starting the inoculation. Air can be sterilized by methods know in the art. For example, the ambient air can pass through at least one filter before being introduced into the vessel. In other embodiments, the medium may be pasteurized or, optionally, no heat at all added, where the use of low water activity and low pH may be exploited to control undesirable bacterial growth.

In one embodiment, the subject invention further provides a method for producing microbial metabolites such as, for example, biosurfactants, enzymes, proteins, ethanol, lactic acid, beta-glucan, peptides, metabolic intermediates, polyunsaturated fatty acid, and lipids, by cultivating a microbe strain of the subject invention under conditions appropriate for growth and metabolite production; and, optionally, purifying the metabolite. The metabolite content produced by the method can be, for example, at least 20%, 30%, 40%, 50%, 60%, 70%, 80%, or 90%.

The microbial growth by-product produced by microorganisms of interest may be retained in the microorganisms or secreted into the growth medium. The medium may contain compounds that stabilize the activity of microbial growth by-product.

The biomass content of the fermentation medium may be, for example, from 5 g/l to 180 g/l or more, or from 10 g/l to 150 g/l.

The cell concentration may be, for example, at least $1 \times 10^6$ to $1 \times 10^{12}$, $1 \times 10^7$ to $1 \times 10^{11}$, $1 \times 10^8$ to $1 \times 10^{10}$, or $1 \times 10^9$ CFU/ml.

The microbial growth by-product produced by microorganisms of interest may be retained in the microorganisms or secreted into the growth medium. The medium may contain compounds that stabilize the activity of microbial growth by-product.

The method and equipment for cultivation of microorganisms and production of the microbial by-products can be performed in a batch, a quasi-continuous process, or a continuous process.

In one embodiment, all of the microbial cultivation composition is removed upon the completion of the cultivation (e.g., upon, for example, achieving a desired cell density, or density of a specified metabolite). In this batch procedure, an entirely new batch is initiated upon harvesting of the first batch.

In another embodiment, only a portion of the fermentation product is removed at any one time. In this embodiment, biomass with viable cells, spores, conidia, hyphae and/or mycelia remains in the vessel as an inoculant for a new cultivation batch. The composition that is removed can be a cell-free medium or contain cells, spores, or other reproductive propagules, and/or a combination of thereof. In this manner, a quasi-continuous system is created.

The microbe-based compositions may be used without further stabilization, preservation, and storage, however. Advantageously, direct usage of these microbe-based compositions preserves a high viability of the microorganisms, reduces the possibility of contamination from foreign agents and undesirable microorganisms, and maintains the activity of the by-products of microbial growth.

In other embodiments, the composition (microbes, growth medium, or microbes and medium) can be placed in containers of appropriate size, taking into consideration, for example, the intended use, the contemplated method of application, the size of the fermentation vessel, and any mode of transportation from microbe growth facility to the location of use. Thus, the containers into which the microbe-based composition is placed may be, for example, from 1 pint to 1,000 gallons or more. In certain embodiments the containers are 1 gallon, 2 gallons, 5 gallons, 25 gallons, or larger.

Advantageously, the method does not require complicated equipment or high energy consumption. The microorganisms of interest can be cultivated at small or large scale on site and utilized, even being still-mixed with their media.

Advantageously, the microbe-based products can be produced in remote locations. The microbe growth facilities may operate off the grid by utilizing, for example, solar, wind and/or hydroelectric power.

Preparation of Microbe-Based Products

In some embodiments, the subject invention provides "microbe-based products," which are products that are to be applied in practice to achieve a desired result. In one embodiment, the microbe-based product of the subject invention is simply the fermentation medium containing the microorganism and/or the microbial metabolites produced by the microorganism and/or any residual nutrients. The product of fermentation may be used directly without extraction or purification. If desired, extraction and purification can be easily achieved using standard extraction and/or purification methods or techniques described in the literature.

Alternatively, the microbe-based product may have components removed, or may comprise further ingredients that have been added. These additional ingredients can include, for example, stabilizers, buffers, appropriate carriers, such as water, salt solutions, or any other appropriate carrier, added nutrients to support further microbial growth, non-nutrient growth enhancers, and/or agents that facilitate tracking of the microbes and/or the composition in the environment to which it is applied. The microbe-based product may also comprise mixtures of microbe-based compositions. The microbe-based product may also comprise one or more components of a microbe-based composition that have been processed in some way such as, but not limited to, filtering, centrifugation, lysing, drying, purification and the like.

The microorganisms in the microbe-based products may be in an active or inactive form, or in the form of vegetative cells, reproductive spores, conidia, mycelia, hyphae, or any other form of microbial propagule. The microbe-based products may also contain a combination of any of these forms of a microorganism.

In one embodiment, different strains of microbe are grown separately and then mixed together to produce the microbe-based product. The microbes can, optionally, be blended with the medium in which they are grown and dried prior to mixing.

In one embodiment, the different strains are not mixed together, but are applied to a plant and/or its environment as separate microbe-based products.

The microbe-based products may be used without further stabilization, preservation, and storage. Advantageously, direct usage of these microbe-based products preserves a high viability of the microorganisms, reduces the possibility of contamination from foreign agents and undesirable microorganisms, and maintains the activity of the by-products of microbial growth.

Upon harvesting the microbe-based composition from the growth vessels, further components can be added as the harvested product is placed into containers or otherwise transported for use. The additives can be, for example, buffers, carriers, other microbe-based compositions produced at the same or different facility, viscosity modifiers, preservatives, nutrients for microbe growth, surfactants, emulsifying agents, lubricants, solubility controlling agents, tracking agents, solvents, biocides, antibiotics, pH adjusting agents, chelators, stabilizers, ultra-violet light resistant agents, other microbes and other suitable additives that are customarily used for such preparations.

In one embodiment, buffering agents including organic and amino acids or their salts, can be added. Suitable buffers include citrate, gluconate, tartarate, malate, acetate, lactate, oxalate, aspartate, malonate, glucoheptonate, pyruvate, galactarate, glucarate, tartronate, glutamate, glycine, lysine, glutamine, methionine, cysteine, arginine and a mixture thereof. Phosphoric and phosphorous acids or their salts may also be used. Synthetic buffers are suitable to be used but it is preferable to use natural buffers such as organic and amino acids or their salts listed above.

In a further embodiment, pH adjusting agents include potassium hydroxide, ammonium hydroxide, potassium carbonate or bicarbonate, hydrochloric acid, nitric acid, sulfuric acid or a mixture.

The pH of the soil treatment composition should be suitable for the microorganism(s) of interest. In a preferred embodiment, the pH of the composition is about 3.5 to 7.0, about 4.0 to 6.5, or about 5.0.

In one embodiment, additional components such as an aqueous preparation of a salt, such as sodium bicarbonate or carbonate, sodium sulfate, sodium phosphate, sodium biphosphate, can be included in the formulation.

In certain embodiments, an adherent substance can be added to the composition to prolong the adherence of the product to plant parts. Polymers, such as charged polymers, or polysaccharide-based substances can be used, for example, xanthan gum, guar gum, levan, xylinan, gellan gum, curdlan, pullulan, dextran and others.

In preferred embodiments, commercial grade xanthan gum is used as the adherent. The concentration of the gum should be selected based on the content of the gum in the commercial product. If the xanthan gum is highly pure, then 0.001% (w/v—xanthan gum/solution) is sufficient.

In one embodiment, glucose, glycerol and/or glycerin can be added to the microbe-based product to serve as, for example, an osmoticum during storage and transport. In one embodiment, molasses can be included.

In one embodiment, prebiotics can be added to and/or applied concurrently with the microbe-based product to enhance microbial growth. Suitable prebiotics, include, for example, kelp extract, fulvic acid, chitin, humate and/or humic acid. In a specific embodiment, the amount of prebiotics applied is about 0.1 L/acre to about 0.5 L/acre, or about 0.2 L/acre to about 0.4 L/acre.

Optionally, the product can be stored prior to use. The storage time is preferably short. Thus, the storage time may be less than 60 days, 45 days, 30 days, 20 days, 15 days, 10 days, 7 days, 5 days, 3 days, 2 days, 1 day, or 12 hours. In a preferred embodiment, if live cells are present in the product, the product is stored at a cool temperature such as, for example, less than 20° C., 15° C., 10° C., or 5° C.

Local Production of Microbe-Based Products

In certain embodiments of the subject invention, a microbe growth facility produces fresh, high-density microorganisms and/or microbial growth by-products of interest on a desired scale. The microbe growth facility may be located at or near the site of application. The facility produces high-density microbe-based compositions in batch, quasi-continuous, or continuous cultivation.

The microbe growth facilities of the subject invention can be located at the location where the microbe-based product will be used (e.g., a citrus grove). For example, the microbe growth facility may be less than 300, 250, 200, 150, 100, 75, 50, 25, 15, 10, 5, 3, or 1 mile from the location of use.

Because the microbe-based product can be generated locally, without resort to the microorganism stabilization, preservation, storage and transportation processes of conventional microbial production, a much higher density of microorganisms can be generated, thereby requiring a smaller volume of the microbe-based product for use in the on-site application or which allows much higher density microbial applications where necessary to achieve the desired efficacy. This allows for a scaled-down bioreactor (e.g., smaller fermentation vessel, smaller supplies of starter material, nutrients and pH control agents), which makes the system efficient and can eliminate the need to stabilize cells or separate them from their culture medium. Local generation of the microbe-based product also facilitates the inclusion of the growth medium in the product. The medium can contain agents produced during the fermentation that are particularly well-suited for local use.

Locally-produced high density, robust cultures of microbes are more effective in the field than those that have remained in the supply chain for some time. The microbe-based products of the subject invention are particularly advantageous compared to traditional products wherein cells have been separated from metabolites and nutrients present in the fermentation growth media. Reduced transportation times allow for the production and delivery of fresh batches of microbes and/or their metabolites at the time and volume as required by local demand.

The microbe growth facilities of the subject invention produce fresh, microbe-based compositions, comprising the microbes themselves, microbial metabolites, and/or other components of the medium in which the microbes are grown. If desired, the compositions can have a high density of vegetative cells or propagules, or a mixture of vegetative cells and propagules.

Advantageously, the compositions can be tailored for use at a specified location. In one embodiment, the microbe growth facility is located on, or near, a site where the microbe-based products will be used (e.g., a citrus grove).

Advantageously, these microbe growth facilities provide a solution to the current problem of relying on far-flung industrial-sized producers whose product quality suffers due to upstream processing delays, supply chain bottlenecks, improper storage, and other contingencies that inhibit the timely delivery and application of, for example, a viable, high cell-count product and the associated medium and metabolites in which the cells are originally grown.

The microbe growth facilities provide manufacturing versatility by their ability to tailor the microbe-based products to improve synergies with destination geographies. Advantageously, in preferred embodiments, the systems of the subject invention harness the power of naturally-occurring local microorganisms and their metabolic by-products to improve agricultural production.

The cultivation time for the individual vessels may be, for example, from 1 to 7 days or longer. The cultivation product can be harvested in any of a number of different ways.

Local production and delivery within, for example, 24 hours of fermentation results in pure, high cell density compositions and substantially lower shipping costs. Given the prospects for rapid advancement in the development of more effective and powerful microbial inoculants, consumers will benefit greatly from this ability to rapidly deliver microbe-based products.

EXAMPLES

A greater understanding of the present invention and of its many advantages may be had from the following examples, given by way of illustration. The following examples are illustrative of some of the methods, applications, embodiments and variants of the present invention. They are not to be considered as limiting the invention. Numerous changes and modifications can be made with respect to the invention.

Example 1—Solid State Fermentation of *Bacillus* Microbes

For *Bacillus* spp. spore production, a wheat bran-based media is used. The media is spread onto stainless steel pans in a layer about 1 to 2 inches think and sterilized.

Following sterilization, the pans are inoculated with seed culture. Optionally, added nutrients can be included to enhance microbial growth, including, for example, salts and/or carbon sources such as molasses, starches, glucose and sucrose. To increase the speed of growth and increase the motility and distribution of the bacteria throughout the culture medium, potato extract or banana peel extract can be added to the culture.

Spores of the *Bacillus* strain of choice are then sprayed or pipetted onto the surface of the substrate and the trays are incubated between 32-40° C. Ambient air is pumped through the oven to stabilize the temperature. Incubation for 48-72 hours can produce $1\times10^{10}$ spores/gram or more of the strain.

Example 2—Solid State Fermentation of Fungal Spores

For growing *Trichoderma* spp., 250 g of nixtamilized corn flour is mixed with deionized water and sterilized in a stainless steel pan, sealed with a lid and pan bands. The corn flour medium is aseptically inoculated with *Trichoderma* seed culture by spraying or pipetting. The pans are then incubated at 30° C. for 10 days. After 10 days, approximately $10^9$ propagules/gram or more of *Trichoderma* can be harvested. *Trichoderma* propagules (conidia and/or hyphae) harvested from one batch can treat, for example, 1,000 to 2,000 acres of land.

Example 3—Preparation of Microbe-Based Product

The microbes, substrate, and any residual nutrients that result from production using the methods described in Examples 1 and 2 can be blended and/or micronized and dried to form granules or a powder substance. Different strains of microbe are produced separately and then mixed together either before or after drying.

A sealable pouch can be used to store and transport a product containing a mixture of $10^9$ cells/g of *T. harzianum* and $10^{10}$ cells/g of *B. amyloliquefaciens*. Micronutrients, or other microbes similarly produced, can be added to the product.

To prepare for use, the dry product is dissolved in water. The concentration can reach at least $5\times10^9$ to $5\times10^{10}$ cells/ml. The product is then diluted with water in a mixing tank to a concentration of $1\times10^6$ to $1\times10^7$ cells/ml.

One bag can be used to treat approximately 20 acres of crop, or 10 acres of citrus grove.

The composition can be mixed with and/or applied concurrently with additional "starter" materials to promote initial growth of the microorganisms in the composition. These can include, for example, prebiotics and/or nanofertilizers (e.g., Aqua-Yield, NanoGro™).

One exemplary formulation of a starter composition comprises:
Soluble potash (K2O) (1.0% to 2.5%, or about 2.0%)
Magnesium (Mg) (0.25% to 0.75%, or about 0.5%)
Sulfur (S) (2.5% to 3.0%, or about 2.7%)
Boron (B) (0.01% to 0.05%, or about 0.02%)
Iron (Fe) (0.25% to 0.75%, or about 0.5%)
Manganese (Mn) (0.25% to 0.75%, or about 0.5%)
Zinc (Zn) (0.25% to 0.75%, or about 0.5%)
Humic acid (8% to 12%, or about 10%)
Kelp extract (5% to 10%, or about 6%)
Water (70% to 85%, or about 77% to 80%).

The microbial inoculant, and/or optional growth-promoting "starter" materials, are mixed with water in an irrigation system tank and applied to soil.

Example 4—Microbial Strains

The subject invention utilizes beneficial microbial strains. *Trichoderma harzianum* strains can include, but are not limited to, T-315 (ATCC 20671); T-35 (ATCC 20691); 1295-7 (ATCC 20846); 1295-22 [T-22] (ATCC 20847); 1295-74 (ATCC 20848); 1295-106 (ATCC 20873); T12 (ATCC 56678); WT-6 (ATCC 52443): Rifa T-77 (CMI CC 333646); T-95 (60850); T12m (ATCC 20737); SK-55 (No. 13327; BP 4326 NIBH (Japan)); RR17Bc (ATCC PTA 9708); TSHTH2O-1 (ATCC PTA 10317); AB 63-3 (ATCC 18647); OMZ 779 (ATCC 201359); WC 47695 (ATCC 201575); m5 (ATCC 201645); (ATCC 204065); UPM-29 (ATCC 204075); T-39 (EPA 119200); and/or F11Bab (ATCC PTA 9709).

*Bacillus amyloliquefaciens* strains can include, but are not limited to, FZB24 (EPA 72098-5; BGSC 10A6), TA208, NJN-6, N2-4, N3-8, and those having ATCC accession numbers 23842, 23844, 23843, 23845, 23350 (strain DSM 7), 27505, 31592, 49763, 53495, 700385, BAA-390, PTA-7544, PTA-7545, PTA-7546, PTA-7549, PTA-7791, PTA-5819, PTA-7542, PTA-7790, and/or PTA-7541.

Example 5—Sod Tensile Strength

Latitude 36 Bermuda sod was treated according to an embodiment of the subject methods. The soil treatment was applied to the sod bi-weekly for a total of 4 treatments.

Figure 2:
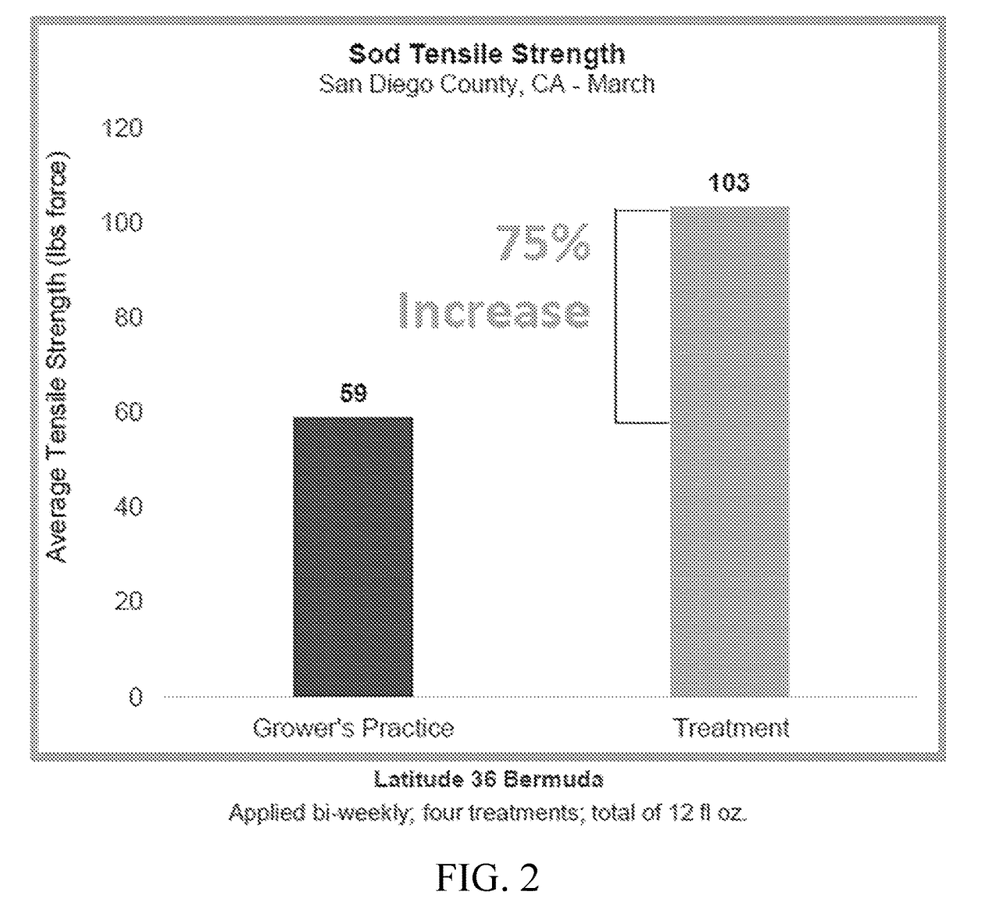
FIG. 2 shows average sod tensile strength (lbs. force) for Latitude 36 Bermuda grass treated according to an embodiment of the subject invention, compared with standard grower's practice (untreated control).

Average tensile strength was measured in lbs. force using a device as shown in FIGS. 1A-1B. An increase of 75% in tensile strength was observed for the treated sod compared with standard grower's practice (control) sod. FIG. 2.

Example 6—Dry Root Mass

Figure 3:
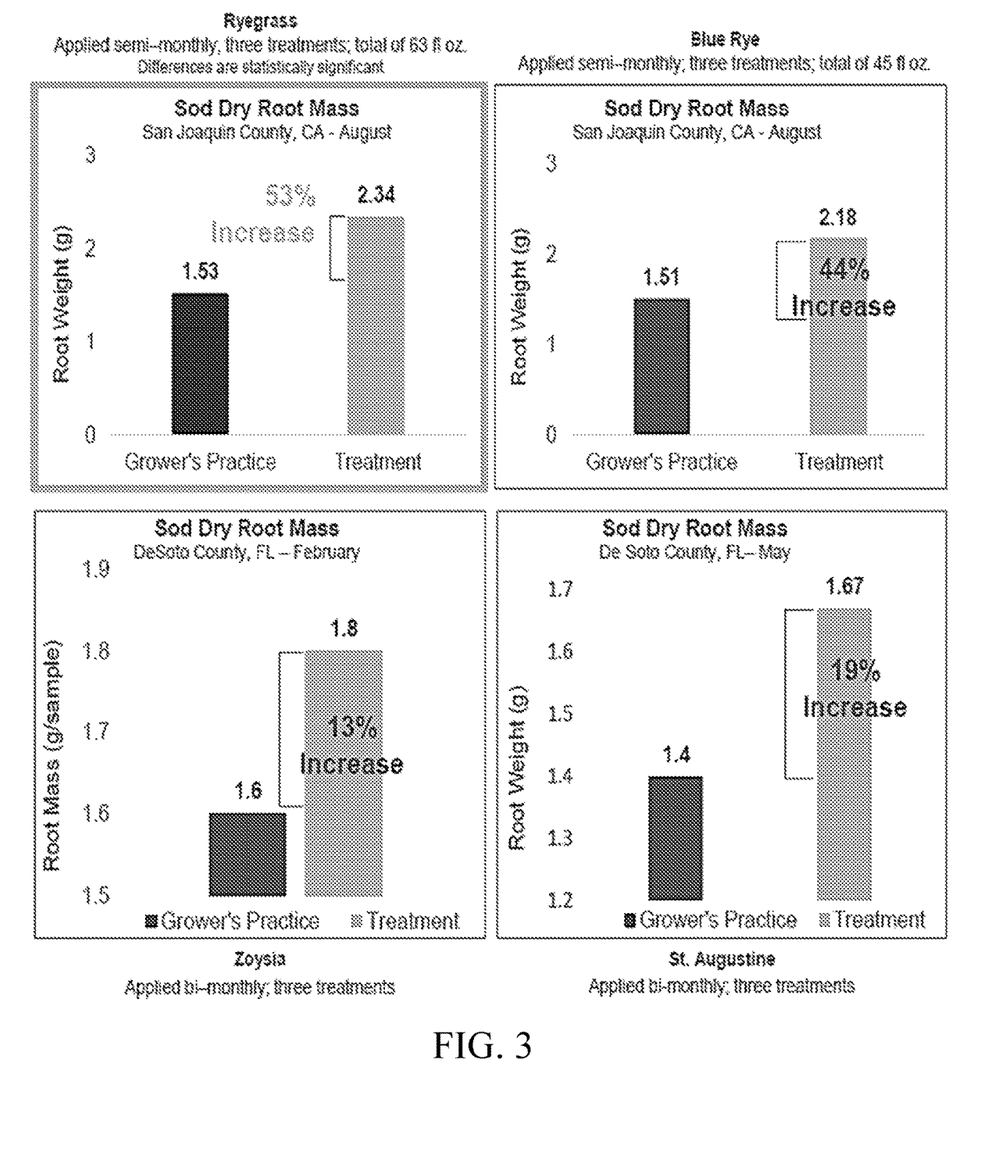

Dry root mass (g) was measured for four types of sod treated according to an embodiment of the subject methods and compared with dry root mass for standard grower's practice (control) sod of the same type. FIG. 3.

Sod was treated three times, either semi-monthly (Ryegrass and Blue Rye) or bi-monthly (*Zoysia* and St. Augustine). A 53% increase in dry root mass was observed for Ryegrass; a 44% increase was observed for Blue Rye; a 13% increase was observed for *Zoysia*; and a 19% increase was observed for St. Augustine sod.

Example 7—Chlorophyll Measurement

Figure 4:
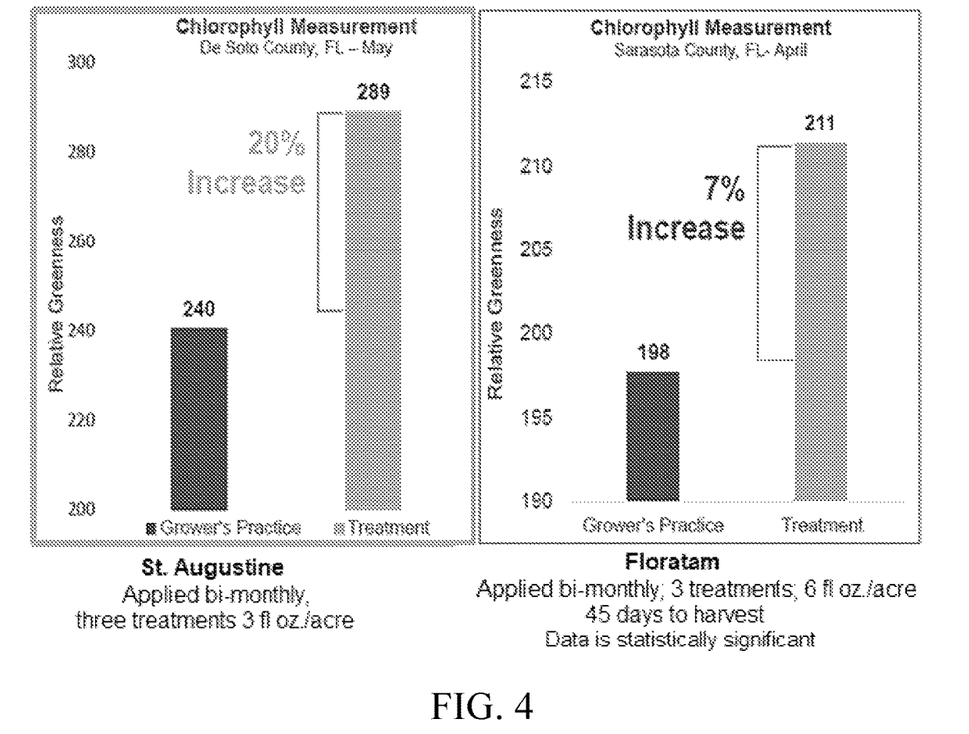
FIG. 4 shows chlorophyll measurement (relative greenness) for St. Augustine sod (left) and Floratam sod (right) treated according to an embodiment of the subject invention, compared with standard grower's practice (untreated control).

Chlorophyll levels were measured for two types of sod treated according to an embodiment of the subject methods and compared with standard grower's practice (control) sod of the same type. FIG. 4.

Sod was treated three times, bi-monthly. The St. Augustine sod treatments were 3 fl. oz./acre each, while the Floratam treatments were 6 fl. oz./acre each. A 20% increase in Relative Greenness was observed for St. Augustine sod; a 7% increase was observed for Floratam sod.

Example 8—Dry Root Mass and Chlorophyll Rating Using *Wickerhamomyces anomalus*

Figure 5A:
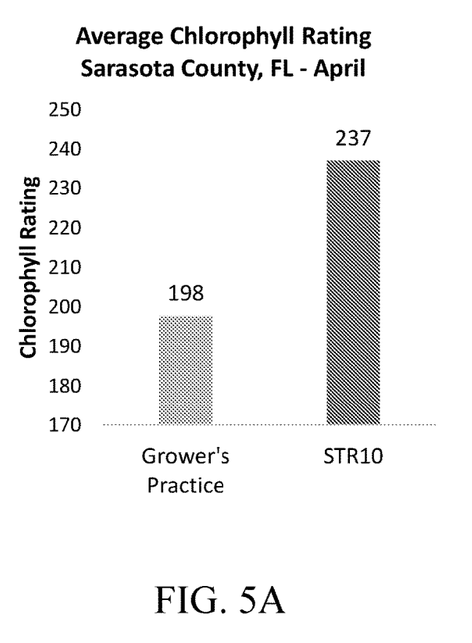
FIGS. 5A-5B show (5A) chlorophyll rating and (5B) dry root mass of St. Augustine grass treated with a soil treatment composition comprising *Wickerhamomyces anomalus* versus control grass.
Figure 5B:
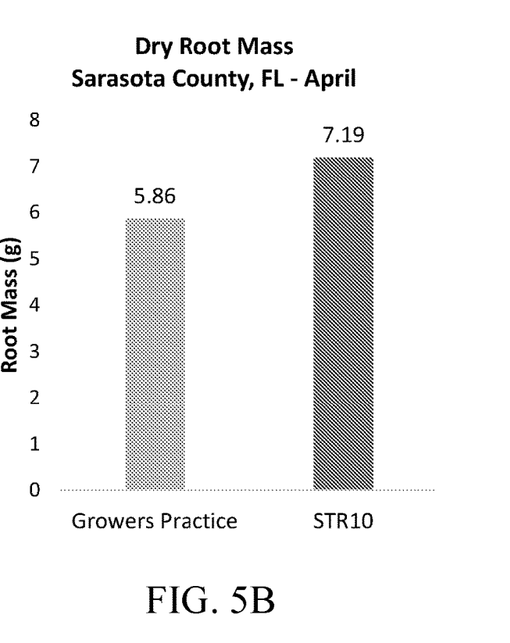

Chlorophyll levels and dry root mass of St. Augustine grass were treated with a soil treatment composition comprising *Wickerhamomyces anomalus* and starter materials according to the formula of Example 3, supra, and compared with standard grower's practice (control) sod of the same type. FIGS. 5A-5B.

Sod was treated three times, bi-monthly, with 1.5 L/acre of the soil treatment composition, and 6.4 fl. oz/acre of the starter materials. A 23% increase in dry root weight and a 20% increase in chlorophyll rating were observed.

Figure 6A:
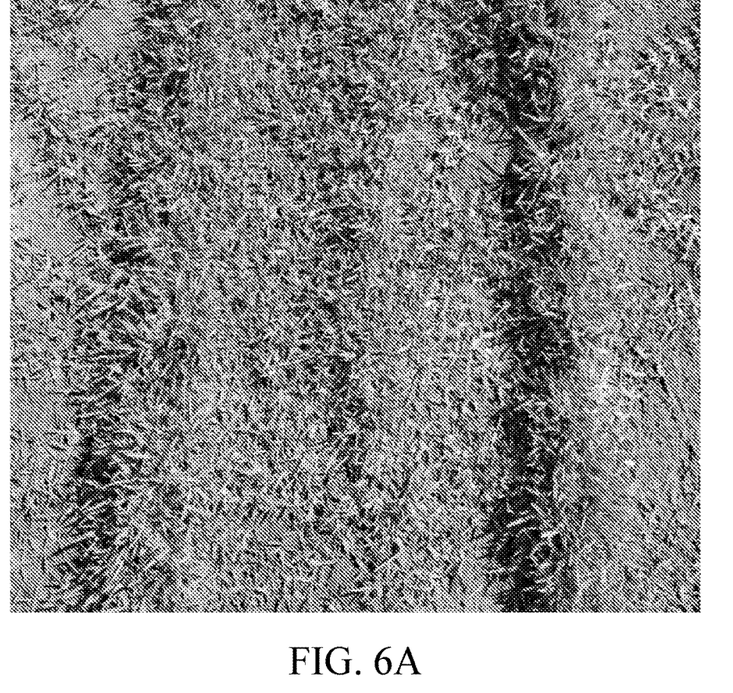
FIGS. 6A-6B show (6A) sow treated with a soil treatment composition comprising *Wickerhamomyces anomalus* and (6B) untreated control sod. Dashed lines indicate bare patches.
Figure 6B:
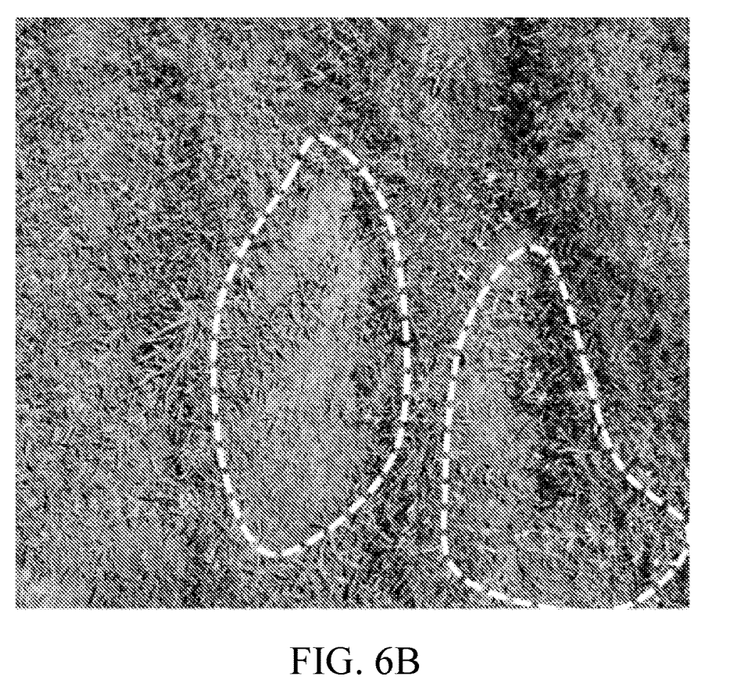

Additionally, as shown in FIGS. 6A-6B, the treated sod showed increased vitality and greater visual appeal, where control grass exhibited bare patches with minimal or no growth of grass.

We claim:

1. A method for enhancing sturdiness of turf grass, the method comprising:
    applying a composition comprising a first microorganism and a second microorganism, one or more growth by-products thereof, and optionally, one or more sources of nutrients, to the roots of the grass and/or to the soil in which the grass grows,
    wherein the first and second microorganisms are non-pathogenic, and
    wherein the first microorganism is *Trichoderma harzianum* and the second microorganism is *Bacillus amyloliquefaciens* NRRL B-67928.

2. The method of claim 1, wherein the first and the second microorganisms are in spore form.

3. The method of claim 1, further comprising applying one or more additional microorganisms and/or growth by-products thereof to the roots and/or to the soil.

4. The method of claim 3, wherein the one or more additional microorganisms are selected from mycorrhizal fungi, *Azotobacter vinelandii, Frateuria aurantia, Myxococcus xanthus, Pseudomonas chlororaphis, Wickerhamomyces anomalus, Starmerella bombicola, Saccharomyces boulardii, Pichia occidentalis, Pichia kudriavzevii,* and *Pichia guilliermondii.*

5. The method of claim 1, further comprising applying one or more of kelp extract, fulvic acid, chitin, humate and humic acid.

6. The method of claim 1, wherein the growth by-products are biosurfactants and/or enzymes.

7. The method of claim 1, wherein the method enhances the strength of the turf grass roots by increasing root density, increasing root diameter, and/or increasing root depth.

8. The method of claim 7, wherein the method further comprises testing the roots of the turf grass to determine the tensile strength of the roots.

9. The method of claim 8, wherein the tensile strength of a sheet of sod is tested by applying tension to the sheet of sod until the sheet tears apart.

10. The method of claim 1, wherein the composition is applied using an irrigation system.

11. The method of claim 1, wherein the composition is applied using a manual spreader, said spreader comprising a broadcast spreader, a drop spreader, a handheld spreader, or a handheld sprayer.

12. The method of claim 1, wherein the grass is in the form of sod comprising the grass plants and a layer of soil held together by the roots of the grass plants and forming a sheet.

13. The method of claim 1, wherein the composition is applied to a field or pitch planted with the turf grass.

14. The method of claim 13, wherein the field is used for athletics and/or recreation.

15. The method of claim 13, wherein the field is a park, campground, amphitheater, golf course, horse track, soccer field, football field, lacrosse field, field hockey field, cricket field, rugby field, polo field, softball field or baseball field.

16. The method of claim 13, wherein the method helps prevent holes and/or divots from occurring in the field as a result of athletic or recreational use.

17. The method of claim 16, used to increase safety of participating in athletics or recreation on the field by preventing injuries caused by stepping in a hole and/or divot.

18. The method of claim 1, wherein the turf grass is annual bluegrass (*Poa annua*); annual ryegrass (*Lolium multiflorum*); Canada bluegrass (*Poa compressa*); Chewings fescue; colonial bentgrass (*Agrostis tenuis*); creeping bentgrass (*Agrostis palustris*); crested wheatgrass (*Agropyron desertorum*); fairway wheatgrass (*Agropyron cristatum*); hard fescue (*Festuca longifolia*); Kentucky bluegrass (*Poa pratensis*); orchardgrass (*Dactylis glomerate*); perennial ryegrass (*Lolium perenne*); red fescue; redtop (*Agrostis alba*); rough bluegrass (*Poa trivialis*); sheep fescue (*Festuca ovine*); smooth bromegrass (*Bromus inermis*); tall fescue (*Festuca arundinacea*); timothy (*Phleum pretense*); velvet bentgrass (*Agrostis canine*); weeping alkaligrass (*Puccinellia distans*); western wheatgrass (*Agropyron smithii*); Bermuda grass (*Cynodon* spp.); St. Augustine grass (*Stenotaphrum secundatum*); zoysia grass; Bahia grass (*Paspalum notatum*); carpet grass (*Axonopus affinis*); centipede grass (*Eremochloa ophiuroides*); kikuyu grass (*Pennisetum clandesinum*); seashore *paspalum* (*Paspalum vaginatum*); floratam (*Stenotaphrum secundatum*); blue gramma (*Bouteloua gracilis*); buffalo grass (*Buchloe dactyloids*); and/or sideoats gramma (*Bouteloua curtipendula*).

\* \* \* \* \*